(12) United States Patent
Bronk

(10) Patent No.: US 8,362,435 B2
(45) Date of Patent: Jan. 29, 2013

(54) METHOD OF CLASSIFYING MICROORGANISMS USING UV IRRADIATION AND EXCITATION FLUORESCENCE

(75) Inventor: Burt V. Bronk, Abington, MD (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 1302 days.

(21) Appl. No.: 12/151,509

(22) Filed: May 7, 2008

(65) Prior Publication Data

US 2012/0161035 A1 Jun. 28, 2012

Related U.S. Application Data

(62) Division of application No. 11/586,742, filed on Oct. 24, 2006.

(60) Provisional application No. 60/729,765, filed on Oct. 24, 2005.

(51) Int. Cl.
*G01J 1/10* (2006.01)

(52) U.S. Cl. ........ 250/362; 250/364; 250/365; 250/369; 250/361 R; 435/34

(58) Field of Classification Search .................. 250/336, 250/361 R, 365, 364, 367, 369, 361 C; 435/7, 435/32, 4, 34; 356/319
See application file for complete search history.

(56) References Cited

U.S. PATENT DOCUMENTS

| | | | |
|---|---|---|---|
| 6,943,346 B2 | 9/2005 | Tan et al. | |
| 2004/0014154 A1 | 1/2004 | Ponce et al. | |
| 2005/0247868 A1* | 11/2005 | Call et al. | 250/282 |
| 2007/0026391 A1* | 2/2007 | Stoughton et al. | 435/5 |
| 2007/0031916 A1 | 2/2007 | Ponce | |
| 2007/0068284 A1 | 3/2007 | Castro et al. | |
| 2008/0093566 A1* | 4/2008 | Reinisch et al. | 250/461.2 |

OTHER PUBLICATIONS

Smith et al. "Detection of *Bacillus* endospores using total luminescence spectroscopy," Spectrochimica Acta Part A, Molecular and Biomolecular Spectroscopy, Bol. 60, Issue 11; published Sep. 2004; pp. 2517-2521. Retrieved from the internet [Aug. 1, 2011]; Retrieved from url <http://www.sciencedirect.com/science/article/pii/S1386142503005912>.*

Bronk et al., "Variability of Steady-State Bacterial Fluorescence with Respect to Growth Conditions," Applied Spectroscopy; Bolume 47, No. 4; pp. 436-440; published 1993.*

Cheng et al., "Detection of Bioaerosols Using Multiwavelength UV Fluorescence Spectroscopy," Aerosol Science and Technology, vol. 20, pp. 186-201, published Feb. 1999. Retrieved from internet [May 14, 2012]; Retrieved from URL <http://dx.doi.org/10.1080/027868299304778>.*

Dalterio et al., "The Steady-State and Decay Characteristics of Primary Fluorescence from Live Bacteria," Applied Spectroscopy, vol. 41, No. 2, published 1987; Retrieved from internet [May 14, 2012]; Retrieved from URL <http://www.opticsinfobase.org/as/asbstract.cfm?uri=as-41-2-234>.*

* cited by examiner

*Primary Examiner* — David Porta
*Assistant Examiner* — Yara Green
(74) *Attorney, Agent, or Firm* — AFMCLO/JAZ; Rebecca Greendyke

(57) ABSTRACT

A method and device for detecting, differentiating from background and providing partial identification (i.e., classification) for biological particles found in aerosols or surface dust. The method is based on the phenomenon that luminescent excitation-emission (EEM) graphs of microorganisms obtained before and after perturbation by irradiation with ultraviolet light show characteristic patterns which differ according to the type of particle. For example, *Bacillus* endospores may be distinguished from vegetative bacteria, and gram positive vegetative bacteria may be distinguished from gram negative bacteria, and all these may be distinguished from many types of background particles, e.g. house dust, road dust, and pollen.

13 Claims, 13 Drawing Sheets

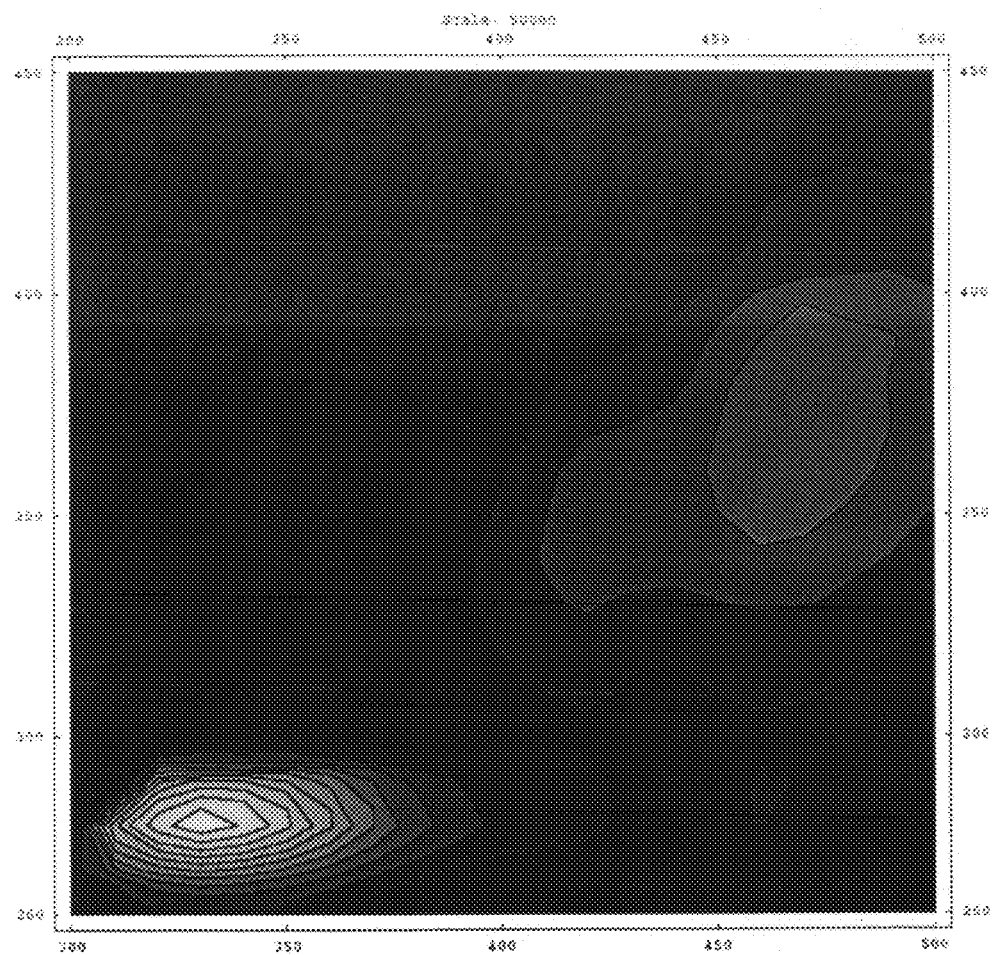
Figure 1. EEM graph for *Bacillus subtilis* spores dried on g-filter. No irradiation. Vertical axis is excitation wavelength, nm. Horizontal axis is emission wavelength, nm. Linear plot.

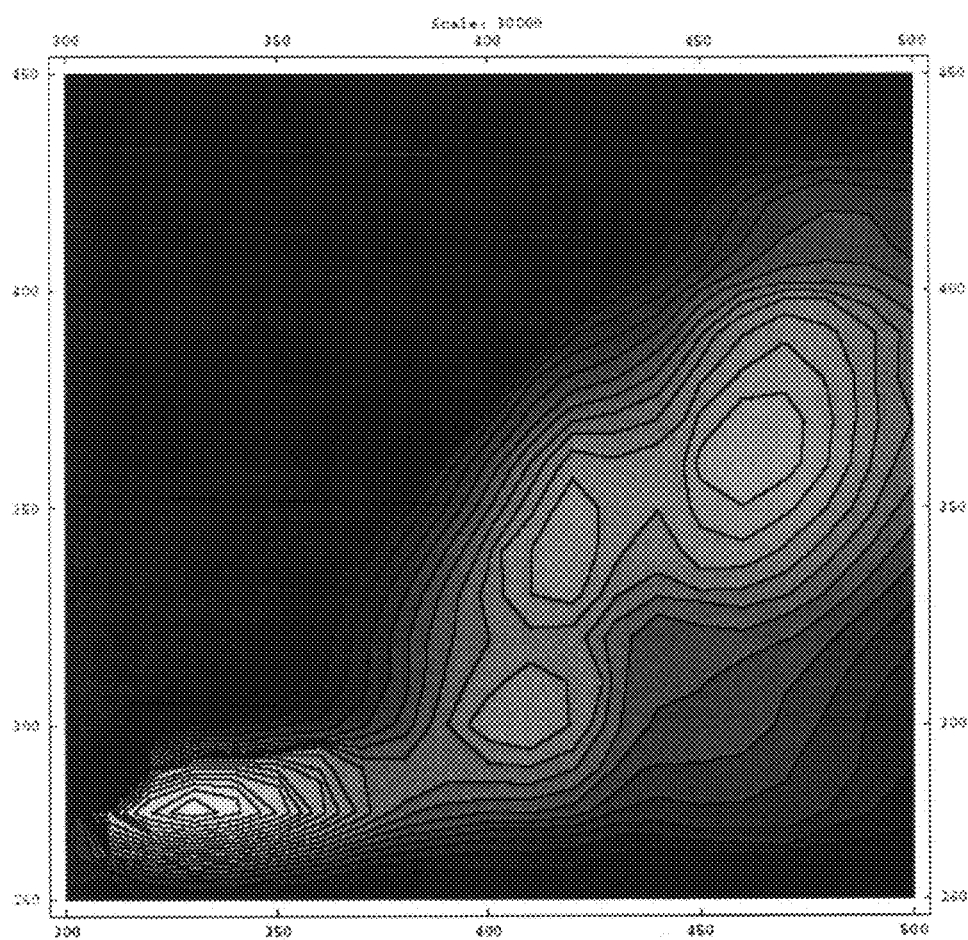
Figure 2 EEM graph for *Bacillus subtilis* spores dried on g-filter after 20 minutes UV irradiation. Linear graph, same axes as Fig 1. Apparent brightness on graph amplified by factor 1.66.

Figure 3 EEM graph for *Bacillus subtilis* spores dried on g-filter. No irradiation. Vertical axis is excitation wavelength, nm. Same experiment as Fig 1 except Horizontal axis is now (emission wavelength)/(excitation wavelength). Nonlinear graph.

Figure 4 EEM graph for *Bacillus subtilis* spores dried on g-filter after 20 minutes UV irradiation. Nonlinear graph, Em/Ex wavelengths ratio, horizontal axis. Apparent graph brightness amplified by factor 1.66.

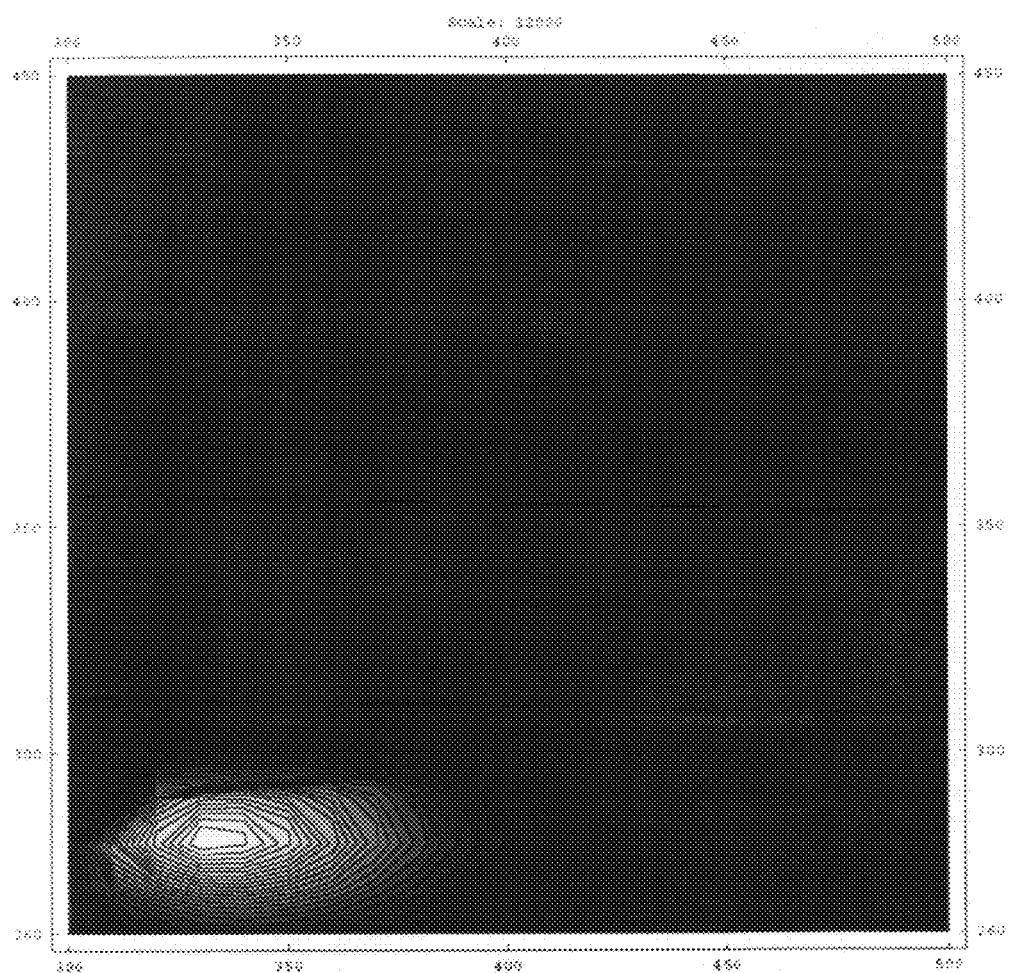
Figure 5 EEM graph for *Escherichia coli* cells dried on g-filter. No UV irradiation. Linear plot (i.e. axes same as Fig 1).

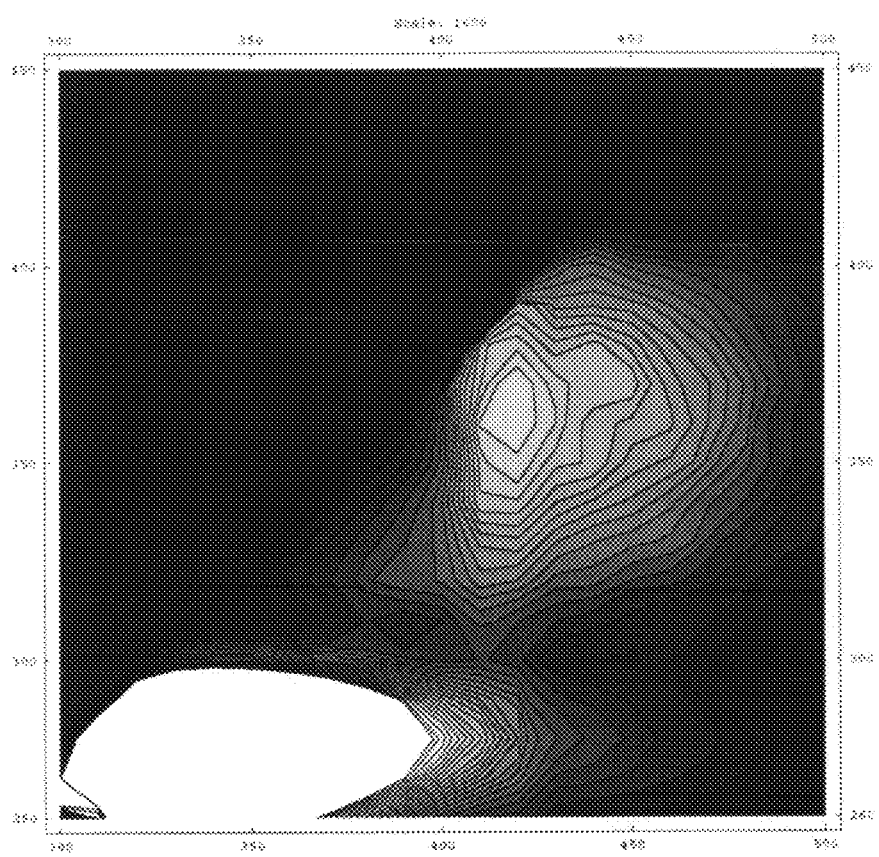
Figure 6 EEM graph for *Escherichia coli* cells dried on g-filter. UV irradiation for 30 minutes. Linear plot (i.e. axes same as Fig 1). Apparent brightness of graph amplified by factor 7.5 from Fig. 5.

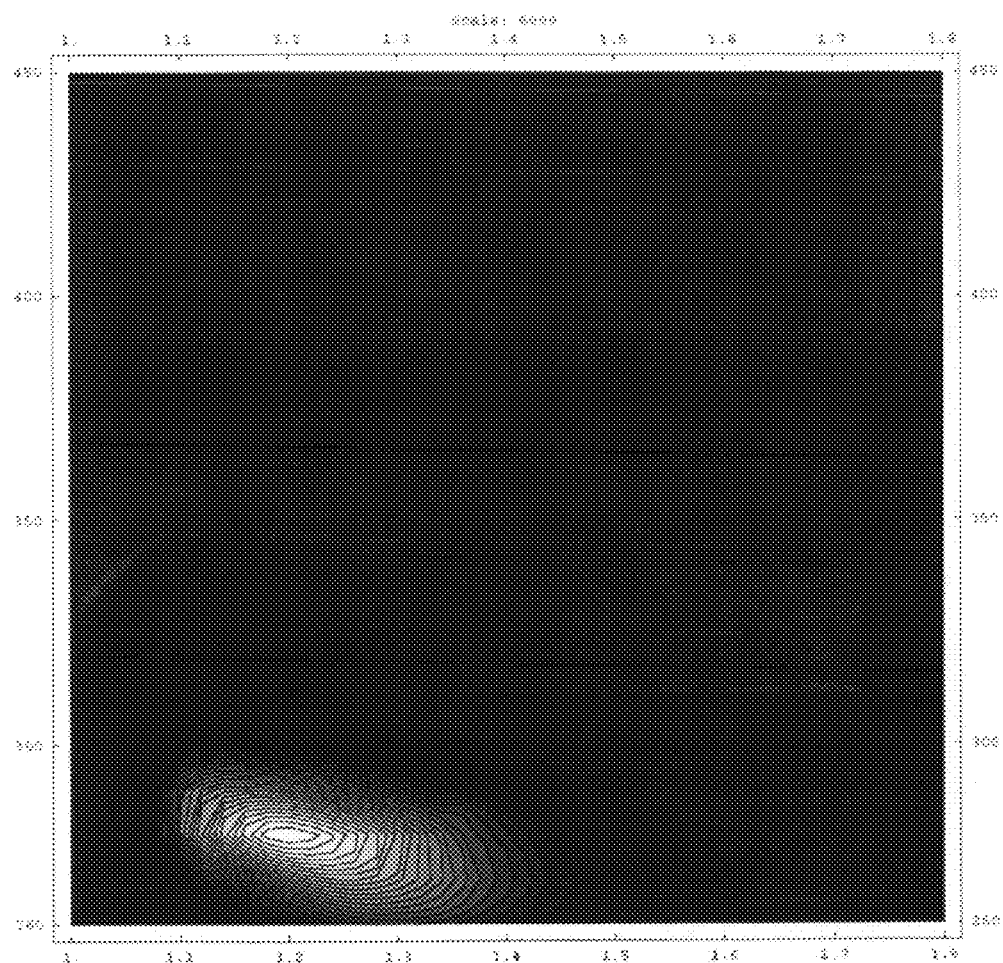
Figure 7 EEM graph for *Escherichia coli* cells dried on g-filter. No UV irradiation. Nonlinear plot (i.e., data same as Fig 5).

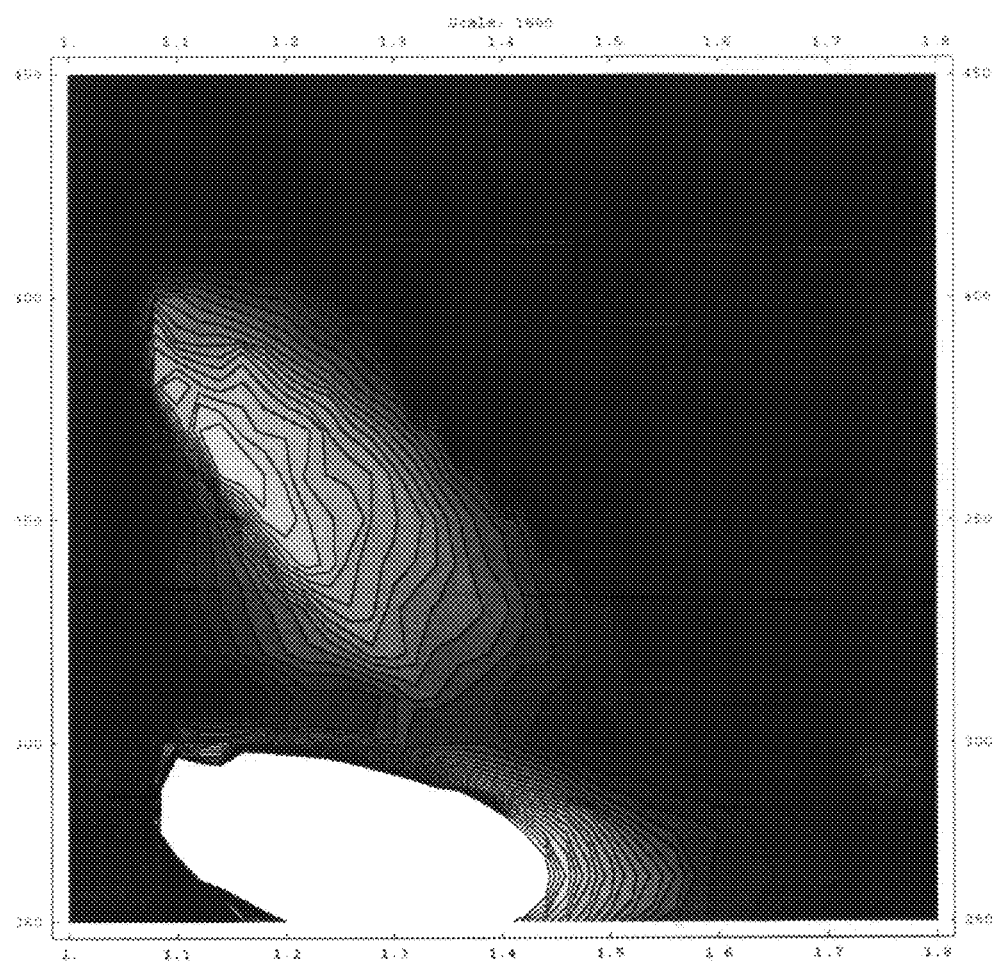
Figure 8 EEM graph for *Escherichia coli* cells dried on g-filter. UV irradiation. for 30 minutes. Nonlinear plot (i.e., data same as Fig 6). Graph brightness amplified by factor 7.5.

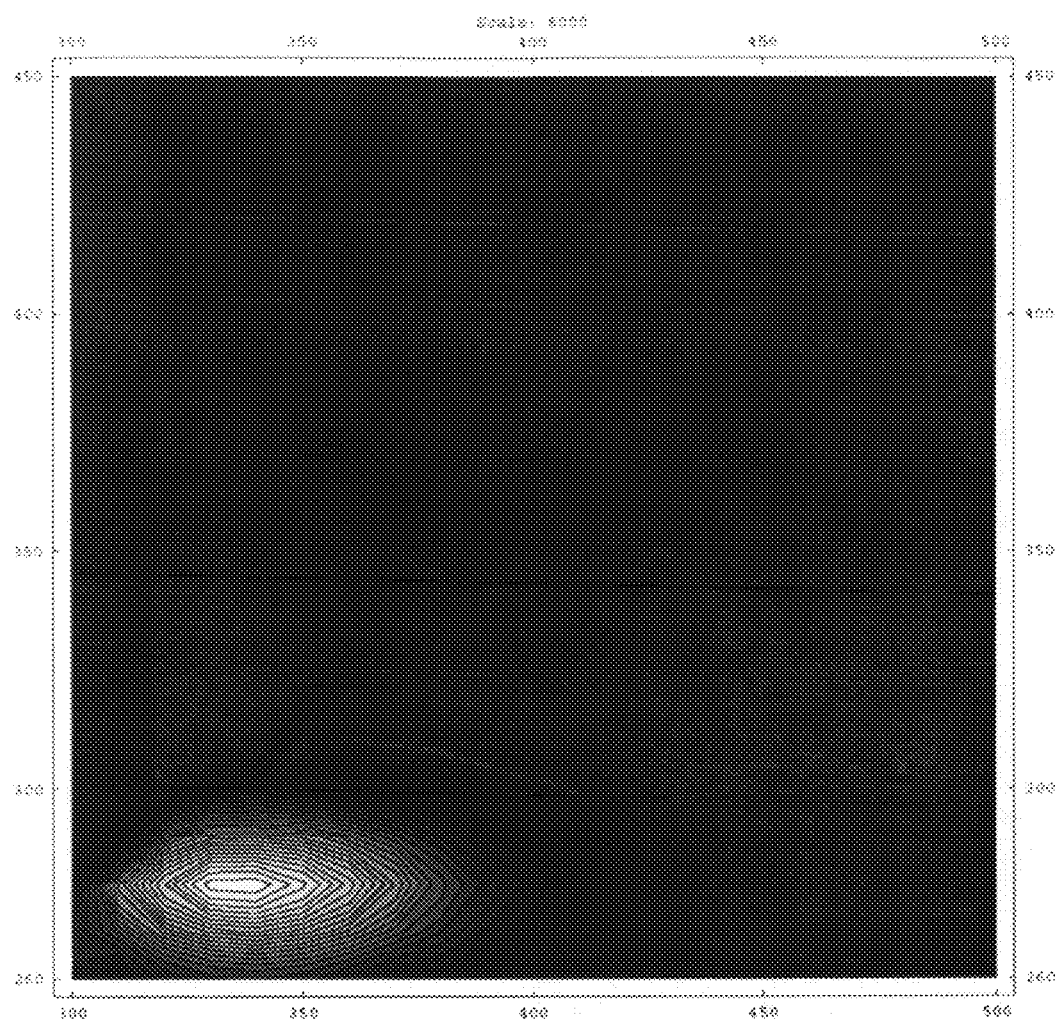
Figure 9 EEM graph for Escherichia coli cells in suspension in 0.03% NaCl solution. No UV. Linear plot.

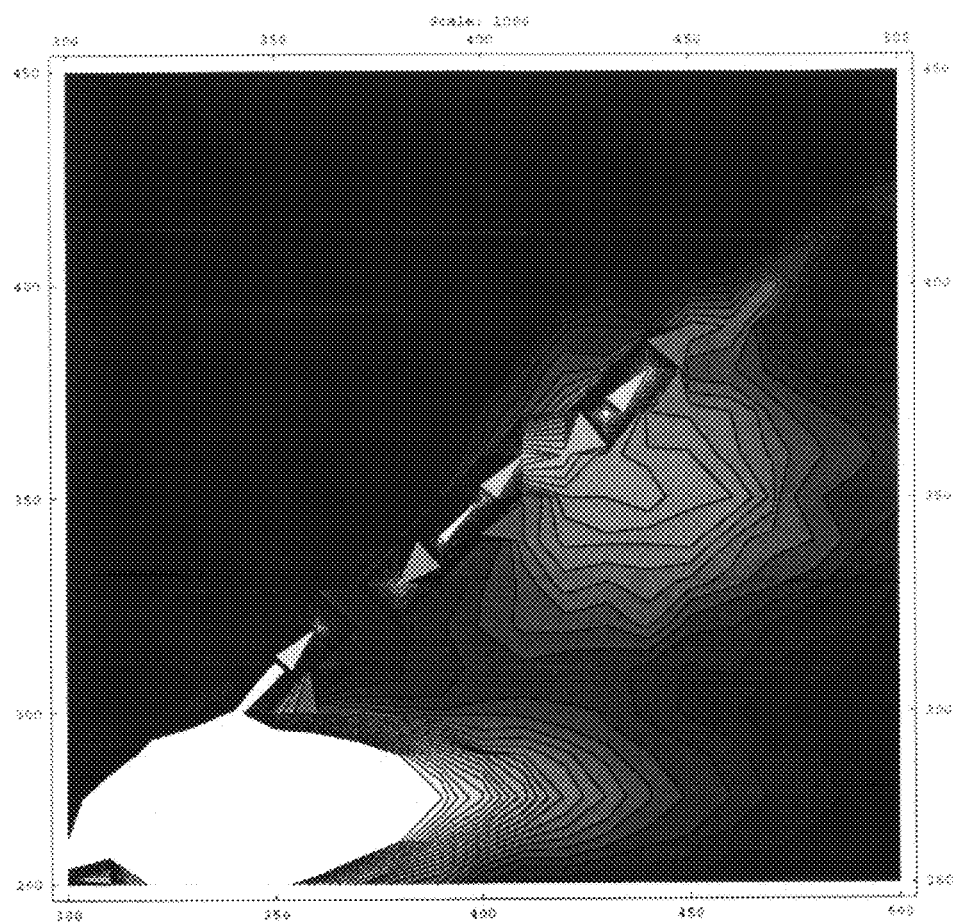
Figure 10 EEM graph of luminescence from suspension of E. coli cells after 30 minutes of UV. Linear plot. Same cells and concentration as Fig. 9 but apparent graph brightness amplified by a factor of six in this graph (e.g., Tryp fluorescence appears saturated on scale of graph).

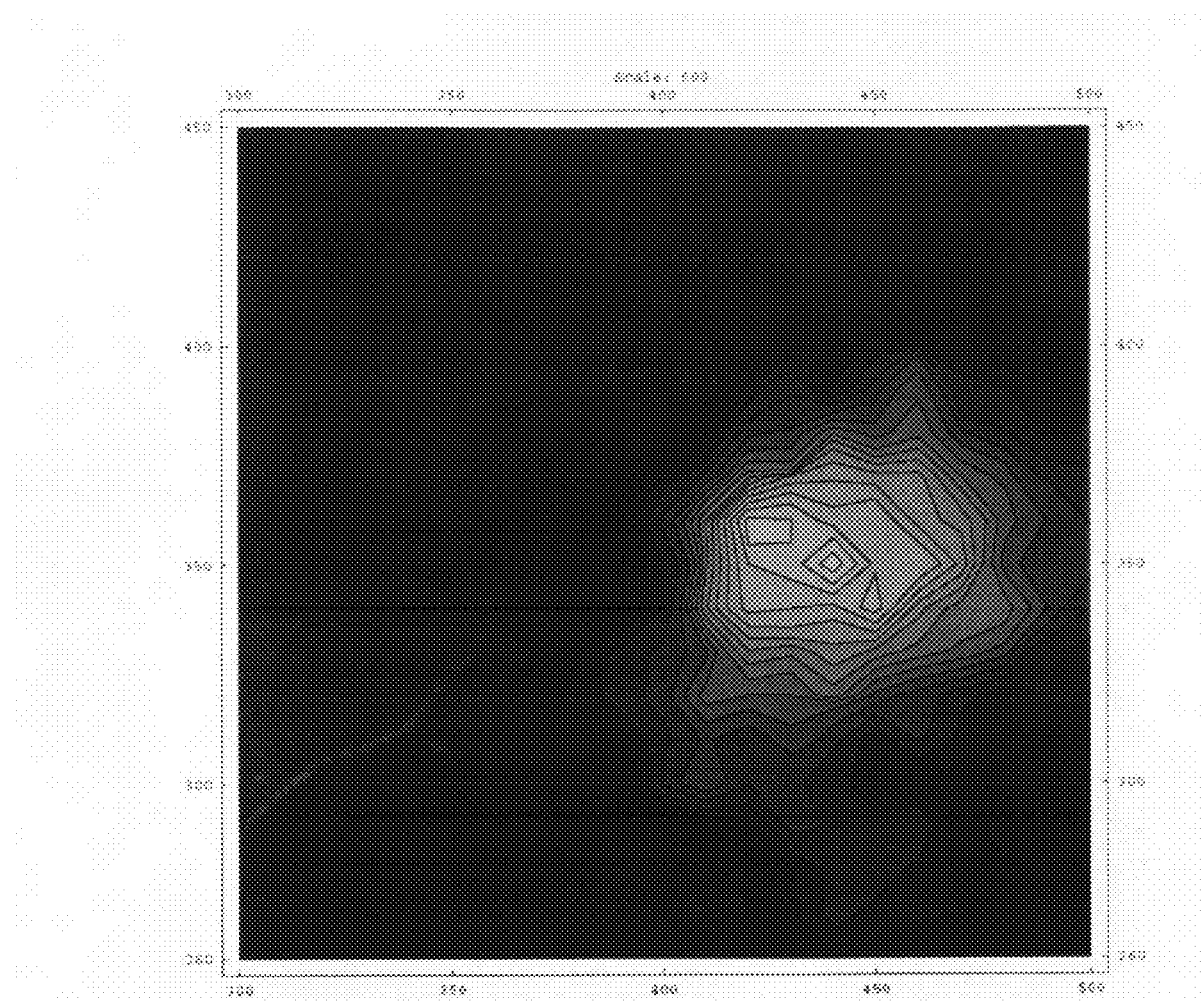
Figure 11 Difference EEM spectrum plotted on scale of Fig.10. Data for Fig 9 is subtracted from data for Fig 10 to remove tryptophan area and eliminate Raman peaks and distortion due to these peaks. Apparent graph brightness amplified by factor of 10 from Fig. 9.

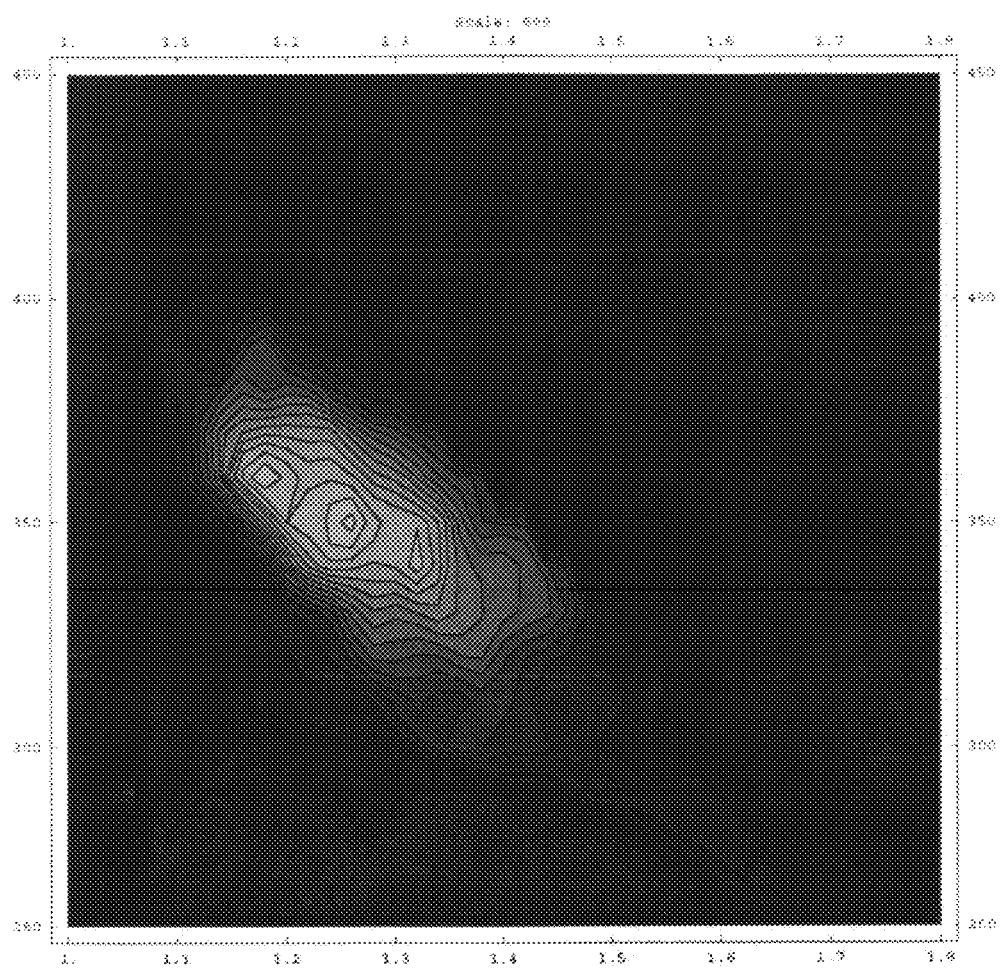
Figure 12. Nonlinear difference EEM graph of same data and scale as Fig 11. Absence of a peak in the CaDPA region is notable (compare references 1, 3, and 4). Apparent graph brightness amplified by factor of 10 from Fig. 9.

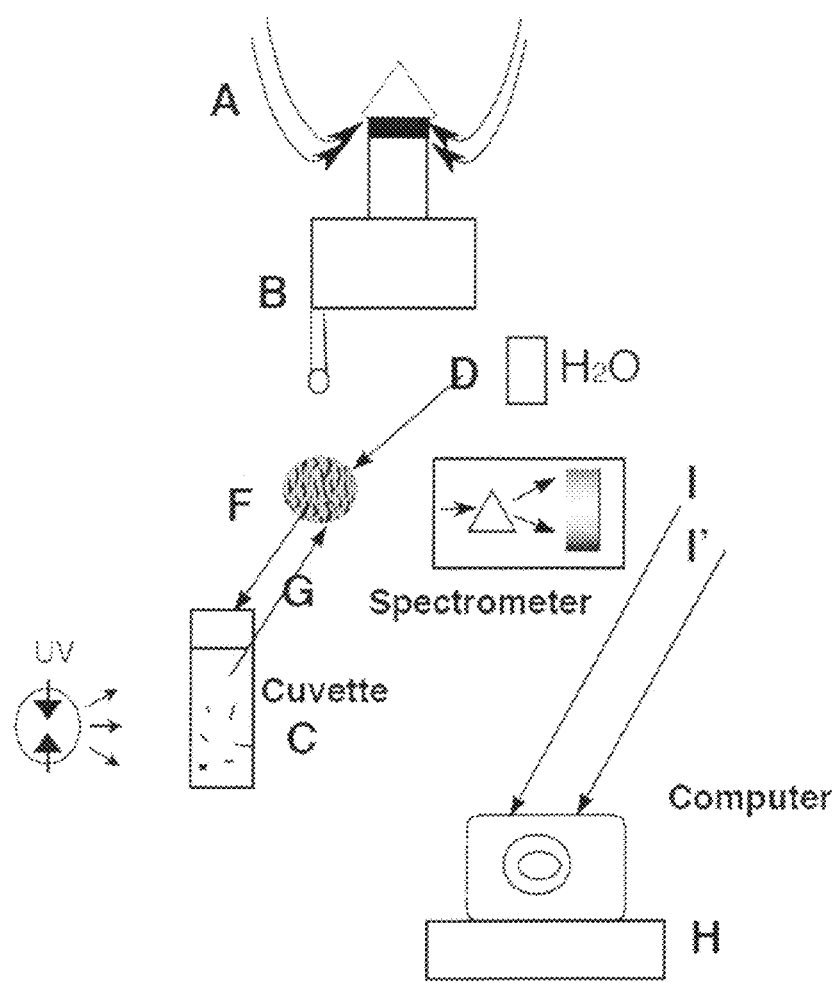
Figure 13: Diagram of steps in typical device incorporating many of the components used in the invention. See description of Method/Device 3.

US 8,362,435 B2

METHOD OF CLASSIFYING MICROORGANISMS USING UV IRRADIATION AND EXCITATION FLUORESCENCE

CROSS REFERENCE TO RELATED APPLICATION

This application is a division of U.S. patent application Ser. No. 11/586,742, filed Oct. 24, 2006 (hereby incorporated by reference), which claims priority of the filing date of Provisional Application Ser. No. 60/729,765, filed Oct. 24, 2005, the entire contents of which are incorporated by reference.

RIGHTS OF THE GOVERNMENT

The invention described herein may be manufactured and used by or for the Government of the United States for all governmental purposes without the payment of any royalty.

BACKGROUND OF THE INVENTION

The invention relates to detection devices and methods, and particularly pertains to the detection and classification of biological particles including bacterial endospores, various species of vegetative bacteria, various harmless background particles etc. This will be accomplished by comparing information extracted from excitation-emission graphs for unknown samples from the environment with information from such graphs obtained from experiments with known samples including but not limited to comparing information from excitation-emission graphs taken from a normal strain graphs taken from a normal strain dipicolonic acid ($DPA^+$) of *Bacillus subtilis* spores and from spores of a mutant strain ($DPA-$) derived from the same $DPA^+$ strain, excitation-emission graphs of the pure chemicals such as CaDPA, DPA and tryptophan which may be components of biological particles. CaDPA and DPA are usually found in bacterial endospores. Further information from excitation-emission graphs taken for various species of vegetative bacteria and for spores from different species of bacteria will also be utilized as well as excitation-emission graphs from various background materials expected to be found at times in aerosols or dust.

When released into the environment, endospores can survive extreme heat, lack of water and exposure to many toxic chemicals and radiation. Most of the water present in the cell cytoplasm is eliminated during spore formation. Such endospores do not generally carry out metabolic reactions. A significantly large amount of the organic acid dipicolonic acid (found in the spore core), is accompanied by a large number of calcium ions. Calcium ions ($Ca.sup.++$) are combined with the dipicolinic acid as seen below.

The calcium-dipicolinic acid complex represents about ten percent of the dry weight of the endospore. As would be understood, such endospores can readily become airborne. If present in an area of human occupancy, such as an office building, home or the like, certain endospores can be life threatening when present through inadvertence, accident or deliberately introduced by bioterrorists.

While various types of detection methods for certain deadly endospores such as *Bacillus anthracis* (anthrax) are known, current methods generally consist of collecting specimens from office buildings, homes or outdoor locations and delivering them to various instruments which at present take from one to several hours or more to complete the analysis. Thus, those unfortunate enough to be exposed to deadly endospores (such as anthrax) or alternatively with other pathogenic bacteria may have the delivery of medical countermeasures significantly delayed so as to exacerbate their condition. Further, rapid early classification such as provided by the present invention can be a trigger to determine where to deliver samples for further interrogation by more time-consuming methods.

Therefore, in view of the need for a speedy and continuous method of detecting anthrax and other pathogenic bacteria, which may be, for example, airborne in public buildings, the present invention was conceived and one of its objectives is to provide a device and method whereby the presence of *bacillus anthracis* or the presence of other classes of bacteria can be easily and inexpensively be indicated as likely.

It is an objective of the invention to provide a device for detecting biological particles when their presence is suspected; for indicating when bacterial endospores are present; and for providing preliminary classification of other bacteria (e.g. Gram positive or Gram negative) when vegetative bacteria are present.

It is another objective of the present invention to provide a device and Method for indicating when bacterial endospores are present; and for providing preliminary classification of other bacteria (e.g. Gram positive or Gram negative) when vegetative bacteria are present which is easy to operate and requires little specialized training.

It is yet another objective of the present invention to provide a method for indicating when bacterial endospores are present and for providing preliminary classification of other bacteria (e.g. Gram positive or Gram negative) when vegetative bacteria are present, both of which are relatively inexpensive to operate continuously for twenty-four hours a day. The invention may optionally comprise triggering an alarm when a suspected biological threat is present. The suspected biological threat may include one or more types of bacterial endospores or vegetative bacteria. Various other objectives and advantages of the present invention will become apparent to those skilled in the art as a more detailed description is set forth below.

SUMMARY OF THE INVENTION

The aforesaid and other objectives are realized by providing a method of screening materials suspected of containing unknown particles including particles down to submicron size. The method comprises providing information contained in at least one or numerous (previously obtained two-dimensional excitation-emission (EEM) type) graphs as would be obtained with a fluorometer, collecting a portion of a sample in powder or liquid suspension form, providing distilled water or other fluids to the sample, delivering a portion of the sample to a cuvette or alternatively a non-fluorescent surface for obtaining EEM graphs of the sample, removing fluids from the sample, generating EEM graphs from the nonirradiated sample, irradiating the sample with Ultraviolet (UV) light (e.g. light of wavelengths between 200 nm and 400 nm), generating an EEM graph after the irradiation, comparing the information from these EEM graphs with each other and with the information contained in previously obtained two-dimensional EEM graphs, removing the sample from the device and preparing the device for a subsequent sample, and determining if the particles in the sample are of biological origin, if they are bacterial endospores, if they are vegetative bacteria, and if they are vegetative bacteria, what large class of bacteria they belong to (e.g., Gram positive or Gram negative).

Further to the present invention, it may be determined with the EEM information whether endospores of *Bacillus* or Clostridia or other genera are present in the sample by comparison of the information from their EEM graphs with those of the stored graphs.

Further to the present invention, it may be determined whether EEM information indicating vegetative bacterial cells are present in the sample and further classifying vegetative bacterial cells made from the EEM information. (e.g., Gram negative from Gram positive).

The objectives of the present invention are further realized with a screening system comprising means for collecting and concentrating a sample, a chamber for washing the sample, non-UV absorbing cuvette for UV irradiation of the sample and/or a nonfluorescent filter on which the sample may be deposited for fluorescent spectrometry with emission measured at a convenient angle, a means for moving the sample (small water and pressure or vacuum source), an ultraviolet light source, an excitation light source or excitation spectrometer, a means of restricting excitation light to desired wavelengths (Excitation spectrometer or broadband light source with filter wheel), an emission spectrometer, a digital or analog medium having stored in it the information from one, several or numerous EEM graphs, a computer, a heating tube for heating the sample (The option of heating may be provided for the purpose of providing additional classification information from EEM graphs taken before and after heating), an aerosol collector concentrator, and a vacuum device or other means of collecting samples from a surface.

The system further includes the option of a screening kit comprising a UV light source, an excitation light source (broadband with filter wheel or excitation spectrometer), an emission spectrometer, a digital medium having stored in it the information from one, several, or numerous EEM graphs, and a computer with appropriate software for comparing the sample EEM graph with information from the stored graphs.

BRIEF DESCRIPTION OF THE DRAWINGS

FIG. 1 is an EEM graph for *Bacillus subtilis* spores dried on g-filter. No irradiation. Vertical axis is excitation wavelength, nm. Horizontal axis is emission wavelength, nm. Linear plot.

FIG. 2 is an EEM graph for *Bacillus subtilis* spores dried on g-filter after 20 minutes UV irradiation. Linear graph, same axes as FIG. 1. Apparent brightness on graph amplified by factor 1.66.

FIG. 3 is an EEM graph for *Bacillus subtilis* spores dried on g-filter. No irradiation. Vertical axis is excitation wavelength, nm. Same experiment as FIG. 1 except Horizontal axis is now (emission wavelength)/(excitation wavelength). Nonlinear graph FIG. 4 is an EEM graph for *Bacillus subtilis* spores dried on g-filter after 20 minutes UV irradiation. Nonlinear graph, Em/Ex wavelengths ratio, horizontal axis. Apparent graph brightness amplified by factor 1.66.

FIG. 5 is an EEM graph for *Escherichia coli* cells dried on g-filter. No UV irradiation. Linear plot (i.e. axes same as FIG. 1.)

FIG. 6 is EEM graph for *Escherichia coli* cells dried on g-filter. UV irradiation for 30 minutes. Linear plot (i.e. axes same as FIG. 1). Apparent brightness of graph amplified by factor 7.5 from FIG. 5.

FIG. 7 is an EEM graph for *Escherichia coli* cells dried on g-filter. No UV irradiation. Nonlinear plot (i.e., data same as FIG. 5)

FIG. 8 is an EEM graph for *Escherichia coli* cells dried on g-filter. UV irradiation for 30 minutes. Nonlinear plot (i.e., data same as FIG. 6). Graph brightness amplified by factor 7.5.

FIG. 9 is an EEM graph for *Escherichia coli* cells in suspension in 0.03% NaCl solution. No UV. Linear plot.

FIG. 10 is an EEM graph of luminescence from suspension of *E. coli* cells after 30 minutes of UV. Linear plot. Same cells and concentration as FIG. 9 but apparent graph brightness amplified by a factor of six in this graph (e.g., Tryp fluorescence appears saturated on scale of graph).

FIG. 11 is a Difference EEM spectrum plotted on scale of FIG. 10. Data for FIG. 9 is subtracted from data for FIG. 10 to remove tryptophan area and eliminate Raman peaks and distortion due to these peaks. Apparent graph brightness amplified by factor of 10 from FIG. 9.

FIG. 12 is a Nonlinear difference EEM graph of same data and scale as FIG. 11. Absence of a peak in the CaDPA region is notable. Apparent graph brightness amplified by factor of 10 from FIG. 9.

FIG. 13 is a Diagram of steps in typical device incorporating many of the components used in the invention.

DETAILED DESCRIPTION OF THE INVENTION

The findings in references (1) B. V. Bronk, L. Reinisch, S. Sarasanandarajah, B. Setlow, and P. Setlow, Studies relating the fluorescence of CaDPA and DPA to the fluorescence of *bacillus* spores" AFRL-HE-WP-TR-2005-0055, 2 May 2005; (2) S. Sarasanandarajah, J. Kunnil, E. Chacko, B. V. Bronk and L. Reinisch, "Reversible changes in fluorescence of bacterial endospores found in aerosols due to hydration/drying" in press J. Aerosol Science (2005); (3) B. V. Bronk, L. Reinisch, and P. Setlow, “The role of DPA in the fluorescence of Bacillus spores”, in CBIAC Report CB-193503, “$6^{th}$ Joint Conference on Standoff Detection for Chemical and Biological Defense” (October 2004), report may be ordered from CBIAC, P.O. Box 196, Aberdeen Proving Ground, Edgewood Area, Gunpowder, Md. 21010-0196, tel: 410-676-9030; and (4) S. Sarasanandarajah, J. Kunnil, B. V. Bronk and L. Reinisch, “Two dimensional multiwavelength fluorescence spectra of dipicolinic acid and calcium dipicolinate”, Appl. Optics, Vol 44, 1182-1187 (2005) indicate that the presence of bacterial endospores is easily detected and differentiated from other unknown micron-sized particles by the changes in the fluorescence Excitation-Emission patterns (EEM displayed on a 2-dimensional contour plot) after the particles are irradiated in the UV as compared to the before irradiation EEM. The source of this irradiation may be either the predominant spectral line from mercury in a germicidal lamp or broadband UV as from a Xenon lamp. The characteristic effect which is seen to the particles EEM pattern occurs in all the following cases:

- when the particles are irradiated dry then examined in a fluorometer for EEM dry
- irradiated dry then examined in a fluorometer wet.
- irradiated wet then dried and examined in a fluorometer for EEM
- irradiated either wet or dry and examined in a fluorometer for EEM in a water or alcohol suspension.

The particles to be examined may be present in the form of an aerosol, dry or wet; a powder found on surfaces; or inside liquid droplets or damp spots found on surfaces which contain micron-sized particles (i.e. particles in the size range ~0.5 micrometers to ~10 or more micrometers); or as micron-sized particles suspended in a liquid.

Endospores (i.e. spores from Bacilli or Clostridia) may be easily distinguished in this manner from vegetative bacteria. Both spores and vegetative bacteria may be distinguished by these means from ambient background such as outdoor and indoor dust, pollen, diesel fuel, smoke and other interferrants.

Further there is some differential classification indicated between different classes of bacteria.

The description refers to the EEM (i.e., Excitation-Emission) graphs shown in the Figures. EEM graphs are shown for both before and after UV irradiation. The irradiation used for the graphs of the Figures is from a mercury bulb emitting primarily at ~254 nm. The dose or amount of irradiation is indicated as minutes of exposure with the intensity measured at the microorganisms approximately equal to 0.85 mW/cm$^2$. For example, irradiation for 20-30 minutes at an intensity of 0.85 mW/cm$^2$ as depicted, for example, in FIGS. 2, 4, 6, 8, and 10 results in a UV dose of about 1 to 1.5 Joules/cm$^2$ (1.02 to 1.53 Joules/cm$^2$). The UV irradiation may optionally be provided by a broadband UV light such as from a Xenon lamp. The UV dose from a broadband light source is about 100 Joules/cm$^2$.

FIG. 1 shows the EEM graph for *Bacillus subtilis* spores dried onto a gold particle filter (reference 8: Schiza, M. V., Perkins, D. L., Ryan, J. P., Setlow, B., Setlow, P., Bronk, B. V., Wong, D. M., and Myrick, M. L., "Improved dispersion of bacterial endospores for quantitative infrared sampling on gold coated porous alumina membranes", Applied Spectroscopy, vol. 59, 1068-1074 (2005)) hereafter referred to as a g-filter. In this experiment the spores were not yet irradiated. All luminescence is referred to as fluorescence although some may be from phosphorescence. The predominant fluorescence is from tryptophan with the peak at excitation near 280 nm. There is a very faint peak for excitation near 370 nm. This peak becomes much stronger after UV irradiation. On all graphs the contours are equally spaced, with the highest luminescence appearing the most white and the least luminescent, the darkest gray or black.

FIG. 2 shows the EEM graph for the same dried spores after 20 minutes UV irradiation from a germicidal lamp. Two new peaks have shown up. One for excitation near 300 nm, and the other for excitation near 340 nm. The peak for excitation near 370 nm has become much stronger. Although it is not apparent from these graphs (scale of the two graphs is not equal), the tryptophan peak for 280 nm excitation has become weaker due to bleaching of the tryptophan molecules. All graphs have their vertical axis as Excitation wavelength in nanometers (nm). All graphs labeled "linear" have their horizontal axis as Emission wavelength.

FIGS. 3 and 4 show graphs corresponding to FIG. 1 and FIG. 2 respectively except that the horizontal axis is now the non-dimensional ratio (emission wavelength)/(excitation wavelength). These plots are called "nonlinear". All the graphs labeled nonlinear have this horizontal axis. The purpose of including the nonlinear versions of the same data is for easier comparison with the graphs in publications which are plotted this way.

FIG. 5 shows the EEM graph for *Escherichia coli* cells grown in LB broth, washed once in PBS buffer and then re-suspended in 0.9% saline and dried onto a g-filter with no UV exposure. The very predominant peak is due to tryptophan (peak excitation near 280 nm) and is very similar in shape to an EEM graph for pure tryptophan (not shown). There is a very much fainter luminescent spot at around 360 nm excitation.

FIG. 6 shows the EEM graph for the same cells and prep, but with the following treatment. A drop of water was put on top to wet the spot of cells, 30 minutes UV irradiation was then applied to the spot on the filter. A luminescent spectrum was then taken after the water dried. The scale has been adjusted to make all emissions appear about 7.5 times brighter on the gray scale in FIG. 6 than for FIG. 5. The tryptophan peak is saturated on this scale. This was done to bring out an apparent change of shape observed for the dimmer spot at about 360 nm excitation.

FIGS. 7 & 8 show the same data as FIGS. 5 & 6 respectively, but with the horizontal axis as Emission/Excitation for comparison with published graphs.

Comparing FIGS. 2 & 4 with FIGS. 6 and 8, it is see that the new luminescence or change for the *E. coli* cells after UV irradiation is quite distinguishable from the new luminescence for *B. subtilis* spores. In particular, the new luminescence for the *E. coli* cells is much fainter compared to their tryptophan fluorescence than is the case for endospores. Further, the shape is different, and the peak near 300 nm excitation attributable to CaDPA is missing from the *E.coli* graphs. This is also the case for *E. coli* fluorescence for cells in suspension (see below).

In the experiment for FIGS. 9 and 10, the *E. coli* cells from the same preparation as for FIG. 5, but suspension was diluted with filtered deionized water to 0.03% NaCl concentration. FIG. 9 shows the EEM linear graph for the unirradiated suspension. Only the tryptophan peak is visible. The shape of the graph indicates that the luminescent region is almost solely attributable to a single chemical. There is a diagonal streak on the graph from lower left to upper right which is due to the water Raman peak. FIG. 10 shows the linear EEM graph for the same suspension after a UV irradiation of 30 minutes. The brightness contours were enhanced by a factor of six making the tryptophan portion appear to saturate the brightness scale. There is additional fluorescence emission at blue wavelengths for excitations near 350 nm. The apparent distortion from smooth contours in FIG. 10 is due to the proximity of bright Raman peaks near the much dimmer *E. coli* fluorescence in this region. A better representation of the contours of this fluorescence in FIG. 11 may be seen when the plotted contours of a difference EEM graph are shown. This graphs the remainder after FIG. 9 subtracted from the data of FIG. 10, and then plotted on the scale of FIG. 10. This eliminates the tryptophan fluorescence region, and the Raman peaks as well as the distortion in the plotting routine caused by the latter. In FIG. 12 the non-linear version of FIG. 11 is plotted. It is notable that the fluorescence of the CaDPA region (refs. 1, 3, and 4) which is prominent in spore fluorescence is much diminished or absent. This makes these vegetative cells easily distinguishable using this method.

The experiments shown here demonstrate that the methods/devices described below can be used to do preliminary classification of unknown particles (e.g., discriminate between several classes of micron-sized particles).

Enabling Methods and Embodiment of Devices Using the Method:

Basically each device will consist of means for exposing the sample to UV irradiation; an excitation-emission fluorometer; means for handling the sample (e.g., adding water if desired); means for transporting a small sample to an observation surface or cuvette; and a computer to record results. The device may optionally be coupled to an alarm that is triggered when a suspected biological threat is detected.

Components, some of which will be used in each of the example devices are listed below. (Not all components will be used in each device). Commercial versions of all the items on the list below exist, but these may need to be redesigned for this application.

Possible Components:

(1) Excitation Source: A source such as a Xenon lamp with strong emission into the UV as well as in the visible. Light at least in the region 250 nm to 550 nm must be available.

(2) UV irradiation source: This may be the same source as (1) but also may be provided by a one or several high intensity mercury lamps (e.g. a germicidal bulb is an inexpensive version) emitting strongly at 254 nm.

(3) Treatment tube for irradiation. This would be a quartz glass tube to allow UV at wavelengths below 300 nm to pass thru to the interior and to hold a liquid suspension. This tube may also act as cuvette if it is desirable to obtain the particle EEM in suspension.

(4) A small excitation spectrometer.

(5) An optical filter wheel and means for changing the band pass center wavelength. This would be used in place of (4) for a simpler less expensive device. The band pass positions may consist of several interference filters or may have continuously changing band pass for a large part of the range.

(6) A small water and pressure or vacuum source for the case when sample is to be immersed and moved in water.

(7) A non-fluorescent tape (e.g. sticky tape) and dispenser which can catch and move the sample in device where sample is not to be wet.

(8) An aerosol collector.

(9) An aerosol concentrator.

10) Emission spectrometer.

(11) A non-fluorescent particle filter to collect particles from water and to provide a surface for taking EEM spectra. An example of such a filter is the gold-coated alumina filter described in reference 8. Its fluorescence has been found to be negligible in unpublished experiments relating to this disclosure.

(12) Vacuum pickup used in place of (8) when it is desirable to collect sample from suspected surfaces and spaces and deposit on filter.

(13) Laptop computer

(14) A means of moving and storing examined particle filter for additional, more time consuming identification (e.g. polymerase chain reaction)

(15) Heating tube. Heat transmitting tube surrounded by resistance heaters.

(16) Rapid Excitation-Emission Fluorometer. This fluorometer combines and replaces (1), (4), and (5) in such a way that the excitation light is spectrally dispersed and each color is directed to a different part of the sample spot. Each individual spot can be contained in a sample less than 1 cm across. The total fluorescence from each fluorescing spot is input to a different position corresponding to excitation wavelength on the slit of an imaging spectrograph. The output is an EEM graph taken in seconds or less.

(17) An input to the emission spectrograph from 90 degree scattering for a selected wavelength, which is attenuated to be comparable to maximum expected fluorescence. This can be directed to a particular position on the imaging spectrograph if properly attenuated.

Situation 1

The main microorganisms to be detected are bacterial spores or vegetative bacteria (eg, powders visible on a surface or from an aerosol suspected in a room or outdoors) then irradiation dry and fluorescence dry may be used.

1$^{st}$ Embodiment

This is the simplest method, to be used to detect spores where there is a visible powder. Instead of an integrated device there would be a kit. The kit would simply consist of a UV light source (2) to irradiate the suspected surface; an excitation light source [component (1) and (5)], and an emission spectrometer [component (11)] to examine emitted light from the suspected surface and a computer with software to compare the EEM graph to a "type-graph" for bacterial spores or other bacterial particles.

Situation 2

The microorganisms are either present in the air as an aerosol, or are deposited on surfaces at a very low concentration.

This is a more sophisticated version of the first embodiment to be used in Situation 2.

2$^{nd}$ Embodiment

An aerosol collector/concentrator [a. components (8) and (9)] or a vacuum pickup, [b. component (12)] would be used continuously. The choice of a. or b. depends on whether an aerosol (a.) or surface dust (b.) is being examined. The concentrator delivers the aerosol sample every 10 minutes into ~5 ml of water which further concentrates the sample into a small spot by being pulled through a non-fluorescent filter [component (11)], leaving all particles greater than the pore size (<1 micrometer) and discarding the liquid. An EEM spectrum is taken on the filter using components (4) and (10). Sample is irradiated [component (2)] on the filter [component (11)], and an EEM spectrum is taken after irradiation with the EEM graphs stored in the computer memory for comparison later.

Small (<100 lbs weight) commercially available versions of these devices [components (8) and (9) combined] typically can concentrate the aerosol from ~400 liters of air per minute into ~5 or 10 ml of water in one minute. We have found ~$10^6$ to $10^8$ organisms in a 10 mm spot on a filter gives a recognizable EEM pattern. Thus if the air contains 1000 organisms/liter as would be typically expected in a deliberate attack, a 10 minute sample on a nonfluorescent particle filter [component (11)] would be adequate.

3$^{rd}$ Embodiment

The diagram for this version is shown in FIG. 13. It is typical of the various devices described. Collection and concentration are as in the second embodiment in an aerosol collector concentrator which concentrates particles in desired size range from a large volume of air (e.g., several hundred liters; see A in FIG. 13) into a small volume of water (e.g. a few ml; see B in FIG. 13). Next the suspended sample is moved to a non-fluorescent filter (F in FIG. 13; component (11)) using component (6) and washed with additional water passing through the sample and filter. EEM spectrum is taken of dried sample on non-fluorescent filter using excitation source, (component (4) not shown) and emission spectrometer (component (10) and spectrometer in FIG. 13). The sample is transferred to small volume of clean water from the filter, and moved into quartz cuvette (C in Fig.; component (3)) for UV irradiation or it may be irradiated on the filter; it is subsequently moved back to filter for a second spectrum. Data defining both EEM spectra are transferred (I and I' in FIG. 13) are transferred to computer (H in FIG. 13, component (13)) for comparison with each other and stored type spectrum. This procedure is typical of the several procedures described in this disclosure. After EEM graphs are examined, particles are washed off filter and transferred out of device to a second filter for storage for further tests (e.g., Polymerase Chain Reaction) or for discarding.

A variation of the third embodiment would take EEM spectra while particles are suspended in water in the quartz tube (C in FIG. 13)

$4^{th}$ Embodiment

Collection and concentration are as in the second embodiment. The particles in suspension are a. heated in component (15)
b. EEM spectrum taken in component (3)
c. UV irradiated in component (3)

The order of application of treatments a., b. and c. will be determined by the treatment which provides maximum differentiation for the classes chosen. EEM graphs are taken with treated sample in cuvette and compared with type graph. with a computer algorithm.

$5^{th}$ Embodiment

This is a variation of the fourth embodiment in which heating and irradiation are in component (15) and (3) but spectra for EEM graphs are taken of particles on a low fluorescence filter as in FIGS. 1 through 12.

$6^{th}$ Embodiment

This is a variation of the other methods in which an attenuated signal (in addition to the EEM spectra) is recorded at a convenient angle from the excitation signal at one or more wavelengths as in component (17). This signal is generally an increasing function of the size of the particles. Its ratio to the tryptophan signal is an additional characteristic of the type of microorganism which will facilitate classification of unknown particles.

I claim:

1. A method of screening comprising:

(a) generating at least one first excitation-emission type graph from at least one known sample, wherein each known sample contains one type of known particle;

(b) irradiation each known sample with ultraviolet light, wherein each known sample receives a first ultraviolet radiation dose of between about 1 to 100 Joules/$cm^2$, the first ultraviolet radiation dose being sufficient to produce at least one detectable change in at least one feature of the excitation-emission type graph;

(c) generating a second excitation-emission type graph from each known sample following the irradiation of step 6(b);

(d) generating at least one first excitation-emission result pattern for at least one unknown sample, wherein each unknown sample contains at least one type of unknown particle;

(e) irradiating each unknown sample with ultraviolet light, wherein each unknown sample receives a second ultraviolet radiation dose of between about 1 to 100 Joules/$cm^2$, the second ultraviolet radiation dose being substantially similar to the first ultraviolet radiation dose, wherein the second ultraviolet radiation dose is sufficient to produce at least one detectable change in at least one feature of the first excitation-emission result pattern;

(f) generating a second excitation-emission result pattern from each unknown sample following the irradiation of step 6(e);

(g) comparing the first excitation-emission result pattern and the second excitation-emission result pattern with one another and with at least one of the first excitation-emission type graph and the second excitation-emission type graph;

(h) determining, based on the comparing of step 6(g), whether microorganisms are present in each unknown sample.

2. The method of claim 1 wherein the first ultraviolet radiation dose and the second ultraviolet radiation dose are generated by a light source capable of emitting a single wavelength selected from a group consisting of 200 to 400 nm.

3. The method of claim 2 wherein the single wavelength is 254 nm.

4. The method of claim 1 wherein the first ultraviolet radiation dose and the second ultraviolet radiation dose are generated by a broadband light source.

5. The method of claim 1 wherein the feature of the first excitation-emission type graph and the feature of the first excitation-emission result pattern each comprise at least one of a location, a magnitude, a breadth, a shape, and an existence of at least one of an individual excitation peak and a peak region.

6. The method of claim 1 wherein the determining in step 6(h) further comprises distinguishing the microorganisms from background particles.

7. The method of claim 6 further comprising distinguishing bacterial endospores from vegetative cells.

8. The method of claim 6 further comprising providing preliminary classification of the microorganisms.

9. The method of claim 6 further comprising determining whether *Bacillus* spores are present.

10. The method of claim 6 further comprising determining whether *Clostridium* spores are present.

11. The method of claim 1 further comprising:

transferring the first and second excitation-emission type graphs and the first and second excitation-emission result patterns to a computer; and comparing, using the computer, the first excitation-emission result pattern and the second excitation-emission result pattern with one another and with at least one of the first excitation-emission type graph and the second excitation-emission type graph.

12. The method of claim 11 further comprising:

continuously monitoring an environment for at least one suspected biological threat, wherein the suspected biological threat includes at least one of a threat bacterial endospore and a threat vegetative bacterial cell; and triggering an alarm when at least one suspected biological threat is identified, wherein the identification includes at least one of detection and classification of the suspected biological threat.

13. The method of claim 1 further comprising concentrating the unknown sample prior to generating the first excitation-emission result pattern

* * * * *